United States Patent [19]

Schwalge et al.

[11] Patent Number: 5,973,001
[45] Date of Patent: Oct. 26, 1999

[54] FUNGICIDAL MIXTURES OF AN OXIME ETHER CARBOXYLIC ACID AMIDE WITH CYMOXANIL

[75] Inventors: Barbara Schwalge, Heidelberg; Ruth Müller, Friedelsheim; Herbert Bayer; Hubert Sauter, both of Mannheim; Eberhard Ammermann, Heppenheim; Gisela Lorenz, Hambach; Siegfried Strathmann, Limburgerhof, all of Germany

[73] Assignee: BASF Aktiengesellshcaft, Ludwigshafen, Germany

[21] Appl. No.: 08/983,558

[22] PCT Filed: Aug. 5, 1996

[86] PCT No.: PCT/EP96/03438

§ 371 Date: Jan. 22, 1998

§ 102(e) Date: Jan. 22, 1998

[87] PCT Pub. No.: WO97/06682

PCT Pub. Date: Feb. 27, 1997

[51] Int. Cl.[6] ............................ A01N 37/18; A01N 37/34
[52] U.S. Cl. ............................................. 514/528; 514/619
[58] Field of Search ..................................... 514/528, 619

[56] References Cited

U.S. PATENT DOCUMENTS 3,957,847  5/1976  Dividson .............................. 260/465.4
5,457,127  10/1995  Wingert et al. ........................ 514/528

FOREIGN PATENT DOCUMENTS

95/18789  7/1995  WIPO .
95/21154  8/1995  WIPO .

OTHER PUBLICATIONS

Research Disc. Jun. 1992, No. 338.
Pesticide Sci., vol. 44, No. 1, May 1995 pp. 77–79.

Primary Examiner—Allen J. Robinson
Attorney, Agent, or Firm—Keil & Weinkauf

[57] ABSTRACT

Fungicidal mixture, comprising
a) an oxime ether carboxamide of the formula I

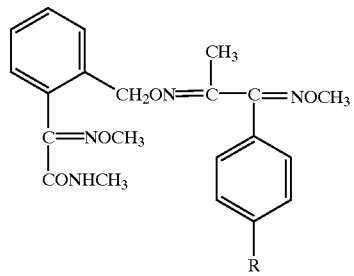

where R is hydrogen or halogen and
b) 1-(2-cyano-2-methoxyiminoacetyl)-3-ethylurea (II)

$$H_3CCH_2-NHCONH-C(CN)=NOCH_3 \qquad II$$

in a synergistically active amount.

6 Claims, No Drawings

FUNGICIDAL MIXTURES OF AN OXIME ETHER CARBOXYLIC ACID AMIDE WITH CYMOXANIL

This application is a 371 of PCT/EP96/03438 filed Aug. 5, 1996.

The present invention relates to a fungicidal mixture which comprises a) an oxime ether carboxamide of the formula I

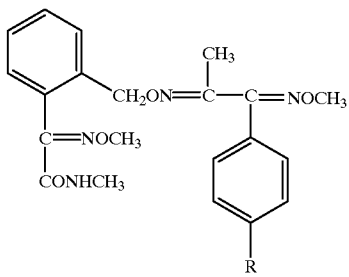

where R is hydrogen or halogen and b) 1-(2-cyano-2-methoxyiminoacetyl)-3-ethylurea (II)

in a synergistically active amount.

Moreover, the invention relates to methods of controlling harmful fungi using mixtures of the compounds I and II and to the use of the compound I and of the compound II for the preparation of such mixtures.

The compound of the formula I, its preparation and its action against harmful fungi are disclosed in the literature (WO-A 95/18,789).

Also disclosed is the compounds [sic] II (U.S. Pat. No. 3,957,847; common name: cymoxanil), its preparation and its action against harmful fungi.

It is an object of the present inventions [sic] to provide mixtures which have an improved action against harmful fungi combined with a reduced total amount of active ingredients applied (synergistic mixtures) with a view to reducing the application rates and to improving the spectrum of action of the known compounds.

Accordingly, we have found that this object is achieved by the mixture defined at the outset. Moreover, we have found that better control of the harmful fungi is possible by applying the compound I and the compound II simultaneously together or separately or by applying the compound I and the compounds [sic] II in succession than when the individual compounds are used.

R in formula I is hydrogen or a halogen atom such as fluorine, chlorine, bromine and iodine, especially hydrogen, fluroine and chlorine, in particular hydrogen or fluorine.

In relation to the C=N double bond, the compounds of the formulae I and II can be present in the E or the Z configuration (in relation to the group [sic] carboxylic acid function). Accordingly, they can each be used in the mixture according to the invention in the form of the pure E or Z isomers or else in the form of an E/Z isomer mixture. The E/Z isomer mixture or the E isomer are preferably used in each case, the E isomer being especially preferred in the case of the compound I.

The C=N double bonds of the oxime ether groups in the side chain of the compounds I can exist in each case in the form of pure E or Z isomers or as E/Z isomer mixtures. The compounds I can be used in the mixtures according to the invention as isomer mixtures or else as the pure isomers. With a view to their use, compounds I which are particularly preferred are those where both oxime ether groups in the side chain are in the E configuration (E/E).

Due to the basic character of the NH group, the compounds I and the compound II are capable of forming salts or adducts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having 1 to 20 carbon atoms), arylsulfonic acids or aryl disulfonic acids (aromatic radicals such as phenyl and naphthyl which have attached to them one or two sulfo groups), alkylphosphonic acids (phosphonic acids having straight-chain or branched alkyl radicals of 1 to 20 carbon atoms), arylphosphonic acids or aryldiphosphonic acids (aromatic radicals such as phenyl and naphthyl which have attached to them one or two phosphoric acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, of the third and fourth main groups, in particular aluminum, tin and lead, and of the first to eighth subgroups, in particular chromium, manganese, iron, cobalt, nickel, copper, zinc and others. Especially preferred are the metal ions of the elements of the subgroups of the fourth period. The metals can exist in the various valencies which they can assume.

When preparing the mixtures, it is preferred to employ the pure active ingredients I and II, with which further active ingredients against harmful fungi or other pests such as insects, arachnids or nematodes, or else herbicidal or growth-regulating active ingredients or fertilizers can be admixed, if so required.

The mixtures of the compounds I and II, or the simultaneous joint or separate use of the compounds I and II, have an outstanding action against a wide spectrum of phytopathogenic fungi, in particular from the classes of the Ascomycetes and Basidiomycetes some of them act systemically and can therefore also be employed as foliar- and soil-acting fungicides.

They are especially important for controlling a large number of fungi in a variety of crop plants such as cotton, vegetable species (eg. cucumbers, beans and cucurbits), barley, grass, oats, coffee, corn, fruit species, rice, rye, soybean, grape vine, wheat, ornamentals, sugar cane and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, Puccinia species in cereals, Rhizoctonia species in cotton and lawns, Ustilago species in cereals and sugar cane, *Venturia inaequalis* (scab) in apples, Helminthosporium species in cereals, *Septoria nodorum* in wheat, *Botrytis cinera* [sic] (gray mold) in strawberries and grape vines, =i Cercospora arachidicolain groundnuts, *Pseudocercosporella*

*herpotrichoides* in wheat and barley, *Pyricularia oryzae* in rice, Phytophthora infestans in potatoes and tomatoes, *Pseudoperonospora Cubense* [sic] in cucurbits,

*Plasmopara viticola* in grape vines, Alternaria species in vegetables and fruit, and Fusarium and Verticillium species.

Furthermore, they can be used in the protection of materials (eg. in the protection of wood), for example against *Paecilomyces variotii*.

The compounds I and II can be applied simultaneously together or separately or in succession, with the order, in the case of separate application, generally not having any effect on the result of the control measures.

The compounds I and II are usually used in a weight ratio of 10:1 to 0.1:1, preferably 5:1 to 0.2:1, in particular 5:1 to 1:1.

The application rates of the mixtures according to the invention are from 0.01 to 3 kg/ha, preferably 0.1 to 1.5 kg/ha, in particular 0.1 to 1.0 kg/ha, depending on the nature of the desired effect. In the case of the compounds I, the application rates are from 0.01 to 0.5 kg/ha, preferably 0.05 to 0.5 kg/ha, in particular 0.05 to 0.4 kg/ha. Accordingly, in the case of the compounds II, the application rates are from 0.01 to 0.5 kg/ha, preferably 0.05 to 0.5 kg/ha, in particular 0.05 to 0.4 kg/ha.

For seed treatment, application rates of the mixture are generally from 0.001 to 50 g/kg of seed, preferably 0.01 to 10 g/kg, in particular 0.01 to 8 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols or of fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenol ether, ethoxylated isooctyl-, octyl- or nonylphenol, alkylphenol polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene [sic], lauryl alcohol polyglycol ether acetate, sorbitol esters, lignosulfite waste liquors or methylcellulose.

Powders, materials for spreading and dusts can be prepared by mixing or jointly grinding the compounds I or II or the mixture of the compounds I and II with a solid carrier.

Granules (eg. coated granules, impregnated granules or homogeneous granules) are usually prepared by binding the active ingredient, or active ingredients, to a solid carrier.

Fillers or solid carriers are, for example, mineral earths, such as silica gel, silicas, silica gels [sic], silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise 0.1 to 95% by weight, preferably 0.5 to 90% by weight, of one of the compounds I and II or of the mixture of the compounds I and II. The active ingredients are employed in a purity of from 90% to 100%, preferably 95% to 100% (according to NMR or HPLC spectrum [sic]).

The compounds-I or II, or the mixtures, or the corresponding formulations, are applied by treating the harmful fungi or the plants, seeds, soils, areas, materials or spaces to be kept free from them with a fungicidally active amount of the mixture, or of the compounds I and II in the case of separate application. Application can be effected before or after infection by the harmful fungi.

Examples of the synergistic action of the mixtures according to the invention against harmful fungi.

The fungicidal action of the compound [sic] and of the mixtures was demonstrated by the following experiments:

The active ingredients, separately or together, were formulated as a 10% strength emulsion in a mixture of 70% by weight of cyclohexanone, 20% by weight of Nekanil® LN (Lutensol® AP6, wetting agent having emulsifying and dispersing action, based on ethoxylated alkylphenols) and 10% by weight of Emulphor® EL (Emulan® EL, emulsifier based on ethoxylated fatty alcohols) and diluted with water to give the desired concentration.

Evaluation was by determining the affected leaf areas in percent. These percentages were converted into efficacies. The expected efficacies of the mixtures of the active ingredients were determined using Colby's formula [R. S. Colby, Weeds 15, 20–22 (1967)] and compared with the observed efficacies.

Colby's formula:

$$E = x + y - x \cdot y / 100$$

E expected efficacy, expressed in % of the untreated control, when using the mixture of the active ingredients A and B at the concentrations a and b x efficacy, expressed in % of the untreated control, when using active ingredient A at a concentration of a y efficacy, expressed in % of the untreated control, when using active ingredient B at a concentration of b The efficacy (E) was calculated as follows using Abbot's formula:

$$E = (1 - \alpha) \cdot 100 / \beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active ingredients were calculated using Colby's formula and compared with the observed efficacies.

Activity against Phytophthora infestans (blight)

Leaves of tomato plants (cultivar "Große Fleischtomate") were first treated with the aqueous preparation of the active ingredients. After approximately 24 hours, the plants were infected with a zoospore suspension of *Phytophthora infestans*. The treated plants were subsequently incubated for 6 days at 16–18° C. and a relative atmospheric humidity of 100%. The extent of the fungal development was subsequently determined.

| Active ingredient | Rate of application [ppm] | Efficacy [%] |
|---|---|---|
| untreated | —/— | 0 |
| I.a (R = H) | 8 | 17 |
|  | 4 | 17 |
| I.b (R = F) | 8 | 27 |
|  | 4 | 27 |
| II | 1 | 90 |
|  | 0.5 | 79 |

| Active ingredient | Rate of application/ mixing ratio | Efficacy Observed | Efficacy Calculated |
|---|---|---|---|
| I.a + II | 8 + 1.0/8:1 | 98 | 92 |
|  | 4 + 0.5/8:1 | 95 | 83 |
| I.b + II | 8 + 1.0/8:1 | 97 | 93 |
|  | 4 + 0.5/8:1 | 97 | 85 |

We claim:

1. A fungicidal composition comprising a) an oxime ether carboxamide compound of the formula I

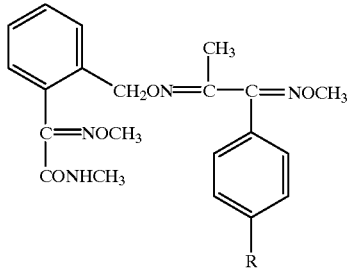

where R is hydrogen or halogen, and b) the 1-(2-cyano-2-methoxyiminoacetyl)-3-ethylurea compound II $$H_3CCH_2—NHCONH—C(CN)=NOCH_3 \quad (II)$$

in a synergistically active amount.

2. The fungicidal composition defined in claim 1, wherein the weight ratio of the compound of the formula I to the compound II is 10:1 to 0.1:1.

3. A method of controlling harmful fungi, which comprises treating the harmful fungi, their environment or the plants, seeds, soils, areas, materials or spaces to be kept free from said fungi with a synergistically effective amount of the compound of the formula I as defined in claim 1 and the compound II as defined in claim 1.

4. The method defined in claim 3, wherein the compound of the formula I and the compound II are applied simultaneously together or separately, or in succession.

5. The method defined in claim 3, wherein from 0.01 to 0.5 kg/ha of the compound of the formula I are applied.

6. The method defined in claim 3, wherein from 0.01 to 0.5 kg/ha of the compound II are applied.

* * * * *